United States Patent
Rodriguez et al.

(10) Patent No.: US 7,332,551 B2
(45) Date of Patent: Feb. 19, 2008

(54) PARTIALLY FLUORINATED NAPHTHYL-BASED BORATES

(75) Inventors: George Rodriguez, Houston, TX (US); Francis C. Rix, League City, TX (US); Periagaram S. Ravishankar, Kingwood, TX (US); Matthew C. Kuchta, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 603 days.

(21) Appl. No.: 10/498,419

(22) PCT Filed: Nov. 12, 2002

(86) PCT No.: PCT/US02/36201

§ 371 (c)(1),
(2), (4) Date: Jun. 10, 2004

(87) PCT Pub. No.: WO03/051892

PCT Pub. Date: Jun. 26, 2003

(65) Prior Publication Data

US 2005/0049436 A1  Mar. 3, 2005

Related U.S. Application Data

(60) Provisional application No. 60/340,662, filed on Dec. 13, 2001.

(51) Int. Cl.
*C08F 4/44* (2006.01)
(52) U.S. Cl. ............... 526/134; 526/160; 502/202; 502/103; 568/6; 568/7
(58) Field of Classification Search ............ 526/134; 502/202, 103; 568/1, 6, 7
See application file for complete search history.

(56) References Cited

U.S. PATENT DOCUMENTS

| | | | |
|---|---|---|---|
| 5,198,401 A | 3/1993 | Turner et al. ........... 502/155 |
| 5,296,433 A | 3/1994 | Siedle et al. ............ 502/117 |
| 5,502,017 A | 3/1996 | Marks et al. ............ 502/103 |
| 6,096,928 A | 8/2000 | Krafft ...................... 568/6 |
| 6,130,302 A | 10/2000 | Marks et al. ............ 526/127 |
| 6,262,200 B1 * | 7/2001 | Marks et al. ............ 526/127 |
| 6,262,202 B1 | 7/2001 | Walzer, Jr. et al. ...... 526/133 |
| 6,437,187 B1 * | 8/2002 | Bohnen et al. ............ 568/9 |
| 6,635,597 B1 * | 10/2003 | Marks et al. ............ 502/202 |
| 6,822,057 B2 * | 11/2004 | Rodriguez ............. 526/133 |

FOREIGN PATENT DOCUMENTS

| | | |
|---|---|---|
| WO | WO/95/24268 | 9/1995 |
| WO | WO 97/29845 | 8/1997 |
| WO | WO 99/06412 A1 * | 2/1999 |

OTHER PUBLICATIONS

Coe et al. J. Chem. Soc. (C), 1971, 604-608.*
Journal of Am. Chem. Soc., Apr. 23, 2001, vol. 123, No. 42, entitled "Efficient, High-Yield Route to Long, Functionalized p-Phenylene Oligomers Containing Perfluorinated Segments, and Their Cyclodimerizations by Zirconocene Coupling", Jonathan R. Nitschke and T. Don Tilley, pp. 10183-10190.
Organometallics 1998, vol. 17, No. 18, entitled "New Organo Lewis Acids. Tris(beta-perfluoronaphthyl)borane (PNB) as highly active Cocatalyst for Metallocene mediated Ziegler natta alpha olefin Polymerization", Liting Li and Tobin J. Marks, pp. 3996-4003.
Newton et al., "Synthesis of Polysilanes Using Group IV Metallocene Based Catalysts and Unusual Boron Based Co-Catalysts," Polymer Preprints, (American Chemical Society, Division of Polymer Chemistry) vol. 39(1), pp. 587-588, (1998). *Abstract.*

* cited by examiner

*Primary Examiner*—Vasu Jagannathan
*Assistant Examiner*—Rip A. Lee

(57) ABSTRACT

Non-coordinating anions or anion precursors are disclosed. These non-coordinating anions serve as the activator for olefin polymerization catalyst systems. As such, they abstract an alkyl leaving group from a metallocene catalyst precursor leaving an activated catalyst charge balanced by a non-coordinating anion. These anions are formed by 3 or 4 partially fluorinated naphthyl ligands coordinated around boron (or other Group-13 element) creating corresponding tris-borane or tetrakis-borate complexes.

18 Claims, No Drawings

PARTIALLY FLUORINATED NAPHTHYL-BASED BORATES

CROSS REFERENCE TO RELATED APPLICATIONS

This application is a National Stage Application of International Application No. PCT/US02/36201, filed Nov. 12, 2002, which claims the benefit of Provisional Application No. 60/340,662, filed Dec. 13, 2001.

TECHNICAL FIELD

This invention relates to the use of noncoordinating anions suitable for stabilizing cationic olefin polymerization catalyst compounds.

BACKGROUND

Noncoordinating anions, in which boron connects to perfluorinated phenyl ligands that increase the anion's lability and stability with respect to un-wanted reactions with the metal cation complexes, are known. (U.S. Pat. No. 5,198, 401). Examples of these include tetrakis(pentafluorophenyl) borate, $[B(PfP)_4]^-$ or $[B(C_6F_5)_4]^-$. Suitable aryl radicals other than phenyl radicals, e.g. naphthyl and anthracenyl, are described. U.S. Pat. No. 5,296,433 describes borane complexes comprising tris(pentafluorophenyl)borane and specific complexing compounds. These complexes polymerize higher molecular weight polymers when used with metallocene catalysts apparently due to their increased monomer or monomer solution solubility. WO 97/29845 describes preparing perfluorobiphenyl borane and using this Lewis acid to prepare and stabilize active olefin-polymerization catalysts. Apparently, these cocatalysts are less coordinating than tris(perfluorophenyl)boron, $B(C_6F_5)_3$ and yield higher catalytic activities. That document describes cocatalysts with the formula BR''' where B is boron, and R' and R'' represent one or more fluorinated biphenyl's or other polycyclic groups, such as naphthyl, anthryl or fluorenyl.

Olefin solution-polymerization processes are generally conducted in aliphatic solvents to maintain reaction temperature and solvate the polymer product. But aryl-group-containing activators dissolve poorly in such solvents. Typically, activators are introduced in toluene or other aryl solvents. Thus, toluene contaminates aliphatic-solvent-based processes. It must be removed because it tends to harm process efficiency. Moreover, aryl-based solvents may be unhealthful in large-scale polymerization and in the resulting polymer. Alternatively, slurries can transport the activators, but that complicates their use and increases plant design costs and operation costs. Low solubility problems are exacerbated when processes involve a low temperature stage, e.g. adiabatic processes run in colder climates. Additionally, separating the solvent or counteracting its build up in the recycle system presents other problems that counter industrial goals. One goal of those is to maintain high polymer molecular weights while operating at high reaction temperatures and high polymer production rates. Therefore, industry desires higher aliphatic solubility for cocatalyst activators.

U.S. Pat. No. 5,502,017 discloses metallocene olefin-polymerization catalysts that contain a weakly coordinating anion based on boron substituted with halogenated aryl or silylallyl substituents, such as tert-butyl-dimethyl-silyl. Apparently, this substitution increases the metallocene salt's solubility and thermal stability. Examples 3-5 describes the synthesis of and polymerization with the cocatalyst: triphenylcarbenium tetrakis (4-dimethyl-t-butylsilyl-2,3,5,6-tetrafluorophenyl)borate.

Thus, a need exists for cocatalyst compounds that improve solution polymerization economics and that provide alternative activators for olefin-polymerization catalyst systems.

SUMMARY

Invention bulky noncoordinating anions are surprisingly stable under polymerization conditions. They allow high-molecular-weight polymer preparation with catalyst efficiencies sometimes exceeding prior art teachings. Thus, the invention is directed to a polymerization process where one or more ethylenically unsaturated monomers are contacted with a catalyst containing at least one organometallic transition metal compound. Before contacting with the monomers, a non-coordinating Group-13 complex activates the transition metal to a cationic state. This Group-13 complex has a Group-13 element tetrahedrally coordinated by partially halogenated polycyclic fused rings. Other invention aspects include non-coordinating activators containing partially halogenated polycyclic fused-rings and catalyst systems that contain such activators. Catalyst systems typically have at least one catalyst precursor and at least one activator. Another aspect of the invention includes a method of making non-coordinating Group-13 element tetrahedrally coordinated by partially halogenated polycyclic fused rings.

DETAILED DESCRIPTION

Invention activating cocatalyst precursors (activators) comprise Group-13 complexes having halogenated aromatic ligands. These ligands contain polycyclic phenyl ring assemblies in which two or more rings are fused to form fused-ring systems. The Group-13 central core connects to these ligands such that the complex has an essentially tetrahedral arrangement around the Group-13 core when anionic, i.e. four coordinating ligands, or an essentially planar arrangement around the Group-13 core when neutral, i.e. three coordinating ligands. Some embodiments select naphthyl as the polycyclic moiety.

A feature of these ring assemblies is that they are partially halogenated or fluorinated. In some embodiments, partial means at least one ring assembly is halogen or fluorine substituted, while at least one ring assembly is not. An exemplary noncoordinating anion has ligands (fused-ring assemblies) as shown below.

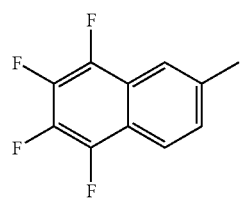

This ligand forms the anion shown below.

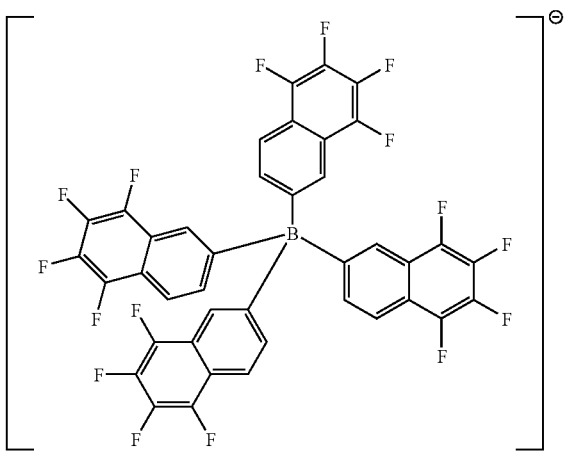

tetrakis(5,6,7,8-tetranaphth-2-yl)borate

Alternatively, the corresponding naphthyl borane may be formed.

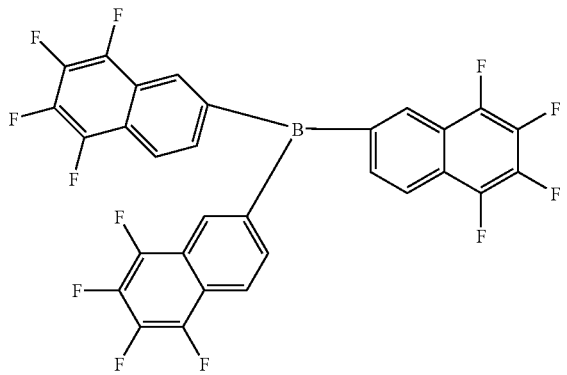

tris(5,6,7,8-tetrafluoronaphth-2-yl)borane

In other embodiments, partially fluorinated or halogenated examples include examples with less than complete fluorination or halogenation on at least one ring and no fluorination or halogenation on at least one ring.

Halogenation or fluorination encompasses fused-ring hydrogen replacement by halogen or fluorine, replacement by a perfluorinated or perhalogenated alkyl, or replacement by a substantially fluorinated or substantially halogenated alkyl. Substantially fluorinated or halogenated means being less than perfluorinated or perhalogenated but fluorinated or halogenated enough to provide a commercially useful improvement over corresponding unfluorinated or unhalogenated species. Put another way, substantially fluorinated means that enough hydrogen atoms have been fluorine-or halogen-replaced so that any remaining hydrogen are not acidic enough to deactivate catalytic sites. While some sites may be deactivated by reaction with hydrogen atoms, not enough sites will be deactivated to harm the catalyst systems' commercial utility.

Transition metal olefin polymerization catalysts for ethylenically unsaturated olefins are typically stable, discrete ionic catalysts. Transition metals include the lanthanide and actinide metals as well as Group-3-10 metals. Transition-metal, olefin-polymerization catalysts are referred to throughout this disclosure variously as transition-metal, olefin-polymerization catalysts; olefin-polymerization catalysts; polymerization catalysts; or simply as catalysts. Their corresponding catalyst precursors are referred to similarly, e.g. transition metal olefin polymerization catalyst precursors.

Invention noncoordinating anions suit all ionic catalyst systems that use NCAs. Suitable transition metal catalysts include those transition metal compounds that polymerize olefins when activated to a cationic state. Suitable processes include those run in homogeneous and heterogeneous, gas-phase, solution, slurry, and bulk polymerization processes to make (co)polymers of ethylenically unsaturated monomer(s): ethylene, propylene, $C_4$-$C_{20}$ $\alpha$-olefins, $C_5$-$C_{20}$ strained-ring cyclic olefins (e.g., norbornene, alkyl-substituted norbornenes), vinyl aromatic monomers (e.g., styrene and alkyl-substituted styrenes), or macromer(s) derived from those monomers. Such processes typically operate from $-50$-$250°$ C. and from 0-3000 bar.

An embodiment of an invention partially fluorinated activator is synthesized using the reaction shown below.

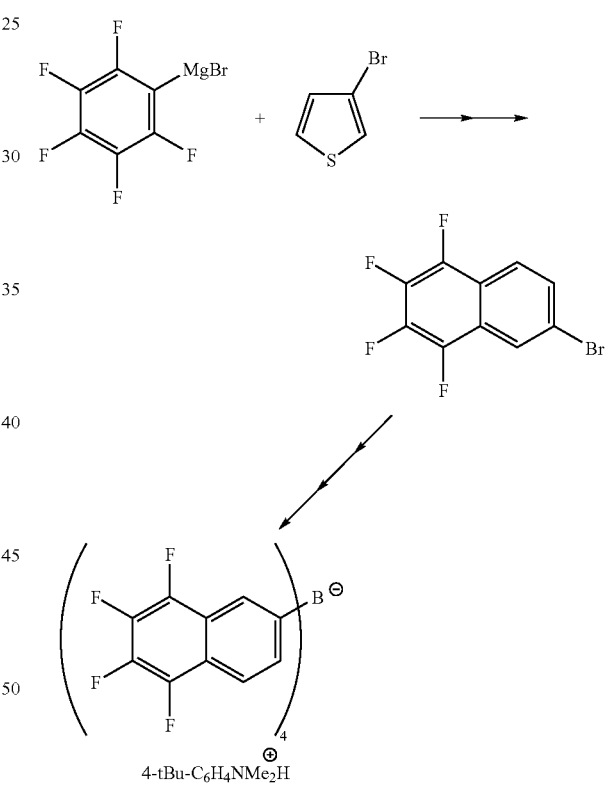

Preparing this borate complex from partially fluorinated naphthyl ligands proceeds at higher yields and at higher purities than complex formation using perfluorinated naphthyl ligands.

Group-4-6 metallocenes exemplify transition-metal, olefin-polymerization catalysts. Metallocenes include (un) bridged compounds containing one (mono(cyclopentadienyl)metallocenes) or two (bis(cyclopentadienyl) metallocenes)(un)substituted cyclopentadienyl ligand(s). In bridged metallocenes, a single, cyclopentadienyl ligand connects to a heteroatom ligand with both coordinating to the metal center, or two cyclopentadienyl ligands connect together with both CP ligands coordinating to the metal center. Typical catalysts and their precursors are well known in the art. Suitable description appears in the patent literature, for example U.S. Pat. Nos. 4,871,705, 4,937,299, 5,324,800, EP-A-0418044, EP-A-0591756, WO-A-92/00333 and WO-A-94/01471. Some embodiments select the metallocene compounds from mono- or bis-CP-substituted, Group-4, -5, and -6 metals in which CPs are (un)substituted with one or more groups or are bridged to each other or to a metal-coordinated heteroatom. Some embodiments select similar metallocene compounds except they are not necessarily bridged to each other or to a metal-coordinated heteroatom. Some higher-molecular-weight polymer-producing embodiments employ bridged biscyclopentadienyl (or substituted biscyclopentadienyl (such as (un)substituted indenyl, (un)substituted fluorenyl, (un)substituted)azulenyl, etc.) rings, and are lower-alkyl-substituted ($C_1$-$C_6$) in the 2 position and additionally contain alkyl, cycloalkyl, aryl, alkylaryl or arylalkyl substituents. Arylalkyl substituents appear either as fused- or pendant-ring structures including multi-ring structures, for example, those of U.S. Pat. Nos. 5,278,264 and 5,304,614.

Metallocene compounds suitable for linear polyethylene or ethylene-containing copolymer production (where copolymer means comprising at least two different monomers) are essentially those disclosed in WO-A-92/00333, WO 97/44370 and U.S. Pat. Nos. 5,001,205, 5,057,475, 5,198,401, 5,304,614, 5,308,816 and 5,324,800. Selection of metallocene compounds for isotactic or syndiotactic polypropylene blend production, and their syntheses, are well-known in the patent and academic literature, e.g. *Journal of Organometallic Chemistry* 369, 359-370 (1989). Typically, those catalysts are stereorigid, asymmetric, chiral, or bridged-chiral metallocenes. Invention activators are suited for activating these types of catalyst precursors.

Likewise, invention activators are suited for activating monocyclopentadienyl metallocenes with Group-15 or -16 heteroatoms connected, through a bridging group, to a Cp-ligand ring carbon Both the Cp-ligand and the heteroatom connect to a transition metal. Some embodiments select a Group-4 transition metal. Additionally, unbridged monocyclopentadienyl, heteroatom-containing Group-4 components of WO 97/22639 will function with this invention. Moreover, transition metal systems with high-oxidation-state, Group-5-10 transition-metal centers are known. These are stabilized by high-oxidation-state, low-coordination-number polyanionic ligands. To the extent that the catalyst precursors are NCA activable, they will function with invention activators, as well.

Non-cyclopentadienyl, Group-4-5 precursor compounds activable to stable, discrete cationic complexes include those containing bulky, chelating, diamide ligands, such as described in U.S. Pat. No. 5,318,935 and "Conformationally Rigid Diamide Complexes: Synthesis and Structure of Tantalum (III)Alkyne Derivatives", D. H. McConville, et al, *Organometallics* 1995, 14, 3154-3156. U.S. Pat. No. 5,318, 935 describes bridged and unbridged, bisamido catalyst compounds of Group-4 metals capable of α-olefins polymerization. Bridged bis(arylamido)Group-4 compounds for olefin polymerization are described by D. H. McConville, et al., in *Organometallics* 1995, 14, 5478-5480. Synthetic methods and compound characterization are presented. Further work appearing in D. H. McConville, et al, *Macromolecules* 1996, 29, 5241-5243, describes bridged bis(arylamido)Group-4 compounds that are polymerization catalysts for 1-hexene. Additional invention-suitable transition-metal compounds include those described in WO 96/40805. Cationic Group-3- or Lanthanide olefin polymerization complexes are disclosed in copending U.S. application Ser. No. 09/408050, filed 29 Sep. 1999, and its equivalent PCT/US99/22690. A monoanionic bidentate ligand and two monoanionic ligands stabilize those catalyst precursors; they are activable with this invention's ionic cocatalysts. Other suitable Group-4-5 non-metallocene catalysts are bimetallocyclic catalyst compounds comprising two independently selected Group-4-5 metal atoms directly linked through two bridging groups to form cyclic compounds.

Suitable Group-10 compounds have a $2^+$ oxidation state. Typical $Ni^{2+}$ and $Pd^{2+}$ complexes are diimines, see "New Pd(II)- and Ni(II)- Based Catalysts for Polymerization of Ethylene and α-Olefins", M. Brookhart, et al, *J. Am. Chem. Soc.*, 1995, 117, 6414-6415, WO 96/23010 and WO 97/02298. See additionally the related bis(imino)Group-8 and -9 organometallic compounds described by V. C. Gibson and others in "Novel olefin polymerization catalysts based on iron and cobalt", *Chem. Commun.*, 849-850, 1998.

Conventional preparations of active transition-metal-non-coordinating-anion catalyst systems are known. Typically, the methods comprise obtaining transition metal compounds with abstractable ligands, e.g., hydride, alkyl or silyl group. Next, the transition metal compound is contacted with a noncoordinating anion or cocatalyst compound in a solvent. The cocatalyst abstracts the univalent hydride, alkyl, or silyl ligand. Abstraction leaves the transition metal compounds with an increased cationic charge, which is counterbalanced by the noncoordinating anion. This activated catalyst system can be introduced into the polymerization reactor in a variety of ways as is known in the art. Moreover, the catalyst precursor and activator can also be contacted with each other inside of the reactor.

Invention noncoordinating anions may be introduced as either ionic compounds having a cation that abstracts one catalyst precursor ligand by protonation or oxidation, or as neutral compounds that directly abstract such a ligand to form a noncoordinating anion. Both ways create a noncoordinating anion. Additionally, alkylating agents can transform non-NCA-abstractable ligands (e.g. transition metal dihalides) into NCA-abstractable ones (e.g. transition metal alkyls). Typically, the strongly Lewis acidic, organoaluminum compounds such as the lower-carbon-number alkyl aluminums and alkylalumoxanes serve as alkylating sources. In situ processes in which alkyl aluminum compounds react with dihalo-substituted metallocene compounds before or upon adding activating anion precursor compounds are known. Some embodiments select transition metal compounds without metal-center halides for catalyst systems, since in situ alkylation may enable competing reactions and interactions that interfere with overall polymerization efficiency under high temperature conditions.

Cation counterparts for invention noncoordinating anion salts include those known in the art for NCAs. Various cation classes include nitrogen-containing cations such as in the anilinium and ammonium salts of U.S. Pat. No. 5,198,401 and WO 97/35893; the carbenium, oxonium, or sulfonium cations of U.S. Pat. No. 5,387,568; metal cations, e.g., $Ag^+$; the silylium cations of WO 96/08519; and those of the hydrated, Group-1 or -2 metal cations of WO 97/22635. Additionally, invention NCAs can come from neutral Lewis acids comprising a Group-13 metal or metalloid center and from one to three halogenated aryl ligands as described above for the invention. Complementary ligands are selected from those known in the art for noncoordinating anions.

The activators of this invention are useful for metallocene catalyst systems that are themselves useful in the polymerization of all types of olefins. This includes polymerization processes that produce homopolymers, copolymers, terpolymers and the like as well as block copolymers and impact copolymers. The polymerization or copolymerization is carried out using olefins of the formula $R^a CH = CH - R^b$. In this formula, $R^a$ and $R^b$ are identical or different and equal a hydrogen atom or a 1-14-carbon-atom-alkyl radical. But $R^a$ and $R^b$ may alternatively form a ring together with the carbon atoms connecting them. Examples of such olefins are ethylene, propylene, 1-butene, 1-hexene, 4-methyl-1-pentene, 1-octene, norbornene and norbornadiene. In particular, propylene and ethylene are polymerized.

Invention catalyst complexes are useful in polymerizing unsaturated monomers known to react under coordination polymerization conditions using metallocenes. For example, polymerization catalysts for olefin polymerization, such as to prepare polyethylene, polypropylene, and copolymers of each. Di-methylsilylbis(indenyl)hafnium dimethyl produces copolyethylene-polypropylene. Diphenylmethylene(cyclopentadienyl)(fluorenyl)hafnium dimethyl polymerizes octene into polyoctene when activated with invention activators. Such conditions are well known and include solution, slurry, gas-phase, and high-pressure polymerizations. Invention catalysts may be supported and, as such, will be particularly useful in the known operating modes employing fixed-bed, moving-bed, fluid-bed, slurry, or solution processes conducted in single, series, or parallel reactors.

Numerous support methods for olefin copolymerization processes are known in the art. Both inorganic oxide and polymeric supports may be used as known in the art.

Methods for supporting ionic catalysts comprising metallocene cations and NCA are described in WO 9950311; U.S. Pat. Nos. 5,643,847; 5,972,823; 6,228,795; and 6,143,686.

Some embodiments first add the NCA to the support composition followed by the addition of the metallocene catalyst. Other methods and order of addition will be apparent to those skilled in the art.

The catalyst systems used to prepare the compositions of this invention are sometimes supported using a porous particulate material, such as for example, talc, inorganic oxides, inorganic chlorides such as magnesium chloride, and resinous materials such as polyolefin or polymeric compounds.

Some embodiments select porous inorganic oxides as the support materials. These oxides include Group-2, -3, -4, -5, -13 or -14 metal/metalloid oxides. Silica, alumina, silica-alumina, and mixtures thereof specific, non-limiting examples of those oxides. Other inorganic oxides that may be employed either alone or in combination with the silica, alumina, or silica-alumina are magnesia, titania, zirconia, and the like.

Some embodiments select the support material as porous silica, which has a surface area of 10-700 m$^2$/g, a total pore volume of 0.1-4.0 cc/g and an average particle size of 10-500 μm. Other embodiments select the surface area to be 50-500 m$^2$/g, the pore volume to be 0.5-3.5 cc/g and the average particle size to be 20-200 μm. Particularly, the surface area is 100-400 m$^2$/g; the pore volume is 0.8-3.0 cc/g; and the average particle size is 30-100 μm. The average pore size of typical porous support materials is 10-1000 Å. Some embodiments select a support material that has an average pore diameter of 50-500 Å, and particularly from 75-350 Å. The silica may be dehydrated at 100° C.-800° C. for from 3-24 hours.

The metallocene, activator, and support material may be combined in any number of ways. More than one metallocene may also be used. Examples of suitable support techniques are described U.S. Pat. Nos. 4,808,561 and 4,701,432. In some embodiments, the metallocenes and activator are combined and their reaction product supported on the porous support material as described in U.S. Pat. No. 5,240,894 and WO 94/ 28034, WO 96/00243, and WO 96/00245. Alternatively, the metallocenes may be preactivated separately and then combined with the support material either separately or together. If the metallocenes are separately supported, they can be dried then combined as a powder before use in polymerization.

Regardless of whether the metallocene(s) and their activator are separately precontacted or whether the metallocene(s) and activator are combined at once, some embodiments select the total volume of reaction solution applied to the porous support to be less than 4 times the total pore volume of the porous support, particularly less than 3 times the total pore volume of the porous support and more particularly from 1-2.5 times the total pore volume of the porous support. Procedures for measuring the total pore volume of porous support are well known in the art. One such method is described in Volume 1, *Experimental Methods in Catalyst Research*, Academic Press, 1968, pages 67-96.

The supported catalyst system may be used directly in polymerization or the catalyst system may be prepolymerized using methods well known in the art. For details regarding prepolymerization, see U.S. Pat. Nos. 4,923,833 and 4,921,825, and EP 0 279 863 and EP 0 354 893.

When using invention catalysts, particularly when support immobilized, the catalyst system will generally additionally comprise one or more scavengers. The term "scavengers" means compounds that remove impurities from the reaction. These impurities adversely affect catalyst activity and stability. In most cases, purification steps are taken before introducing the feeds into the reaction vessel. But small scavenging compound amounts will normally be used in the polymerization process. Where possible, alkylaluminum scavenging compounds are avoided altogether.

Typically, the scavenger will be an organometallic compound such as the Group-13 organometallic compounds of U.S. Pat. Nos. 5,153,157, 5,241,025 and WO-A-91/09882, WO-A-94/03506, WO-A-93/14132, WO 95/07941 and of WO 97/22635. Exemplary compounds include triethyl aluminum, triethyl borane, triisobutyl aluminum, methylalumoxane, isobutyl aluminumoxane, tri(n-octyl) aluminum and tri(n-octyl)aluminum. Those scavengers having bulky or $C_6$-$C_{20}$ linear hydrocarbyl substituents covalently bound to the metal or metalloid center usually to minimize adverse interaction with the active catalyst. Examples include triethylaluminum, bulky compounds such as triisobutylaluminum, triisoprenylaluminum, and long-chain linear-alkyl-substituted aluminum compounds, such as tri-n-hexylaluminum, tri-n-octylaluminum, or tri-n-dodecylaluminum. Alumoxanes also may be used in scavenging amounts, e.g., methylalumoxane and triisobutyl-aluminoxane. Invention processes minimize the scavenger amount during polymerization reactions to that amount effective to enhance activity and avoid them altogether if the feeds are sufficiently impurity free.

Some invention embodiments employ catalyst systems in liquid phase (solution, slurry, suspension, bulk phase or their combinations), in high-pressure-liquid or supercritical-fluid phase, or in gas phase. Singular, parallel, or series reactors suit these processes. The liquid processes comprise contacting olefin monomers with the described catalyst systems in suitable diluents or solvents and comprise allowing those monomers to react long enough to produce invention copolymers, both aliphatic and aromatic ones. Hydrocarbyl solvents are suitable. Some embodiments select hexane and toluene. Halocarbon solvents, such as methylene chloride are also suitable. Some embodiments use other solvents such as aliphatic, cycloaliphatic or aromatic hydrocarbons. Some embodiments select solvents with $C_{12}$ or lower, straight-chain or branched-chain, saturated hydrocarbons, and $C_5$-$C_9$, saturated alicyclic or aromatic hydrocarbons. Examples of such solvents or reaction media are hexane, butane, pentane, heptane, cyclopentane, cyclohexane, cycloheptane, methyl cyclopentane, methyl cyclohexane, isooctane, benzene, toluene, xylene and their mixtures. In addition, one or more olefins, either alone or mixed with other media, may serve as the reaction media, at selected olefin concentrations. Bulk and slurry processes typically include contacting the catalysts supported with liquid monomer or with monomer in liquid alkane.

Gas-phase coordination polymerizations typically use a supported cata-lyst and are conducted in any suitable manner for ethylene homo- or co-polymerization.

Generally speaking, polymerization reaction temperatures vary from −50° C.-250° C. Some embodiments select the reaction temperature from −20° C.-220°; other embodiments select the reaction temperature below 200° C. Pressure ranges from about 0.001-3000 bar. Some embodiments select pressure from 0.1 bar-2000 bar. Molecular weight, tacticity, and stereo- and regio-defect levels depend on reactor temperature. Thus, desired values for these properties guide reactor temperature selection. The reactors may be cooled by reactor jackets, cooling coils, auto refrigeration, pre-chilled feeds, or their combinations. Some embodiments select adiabatic reactors with pre-chilled feeds.

In some embodiments, processes using unsupported catalysts are designed or conducted such that the transition metal compounds and the anion precursor compounds are kept apart. They are mixed in the reactor or immediately before reactor injection. An example is dual injection of each catalyst component directly into the reactor. Another is premixing with T- or multi-joint mixing chambers just before reactor injection. Alternatively, some embodiments employ in-situ-formed catalyst prepared by adding ionic activator, ligand-stabilized metal-halide catalyst precursor, and scavenger directly into the reactor or into the T- or multi-joint mixing chambers for pre-injection preparation. Some embodiments call for scavenger injection separate from catalyst system or catalyst compound injection.

The following metallocene catalysts are activable by invention partially fluorinated discrete activators:

(benzylcyclopentadienyl)(cyclopentadienyl)hafnium dihydride; (benzylcyclopentadienyl)(cyclopentadienyl)hafnium dimethyl; (benzylcyclopentadienyl)(cyclopentadienyl)titanium dihydride; (benzylcyclopentadienyl)(cyclopentadienyl)titanium dimethyl; (benzylcyclopentadienyl)(cyclopentadienyl)zirconium dihydride; (benzylcyclopentadienyl)(cyclopentadienyl)zirconium dimethyl; (cyclohexylmethylcyclopentadienyl) (cyclopentadienyl)hafnium dimethyl; (cyclohexylmethylcyclopentadienyl)(cyclopentadienyl)titanium dimethyl; (cyclohexylmethylcyclopentadienyl)(cyclopentadienyl)zirconium dimethyl; (cyclohexylmethylcyclopentadienyl)(cyclopentadienyl)hafnium dihydride; (cyclohexylmethylcyclopentadienyl)(cyclopentadienyl)titanium dihydride; (cyclohexylmethylcyclopentadienyl)(cyclopentadienyl)zirconium dihydride; (dimethylcyclopentadienyl)(cyclopentadienyl)hafnium dihydride; (dimethylcyclopentadienyl)(cyclopentadienyl)hafnium dimethyl; (dimethylcyclopentadienyl)(cyclopentadienyl)titanium dihydride; (dimethylcyclopentadienyl)(cyclopentadienyl)titanium dimethyl; (dimethylcyclopentadienyl)(cyclopentadienyl)zirconium dihydride; (dimethylcyclopentadienyl)(cyclopentadienyl)zirconium dimethyl; (diphenylmethylcyclopentadienyl)(cyclopentadienyl) hafnium dimethyl; (diphenylmethylcyclopentadienyl)(cyclopentadienyl)titanium dimethyl; (diphenylmethylcyclopentadienyl)(cyclopentadienyl)zirconium dimethyl; (diphenylmethylcyclopentadienyl)(cyclopentadienyl) hafnium dihydride; (diphenylmethylcyclopentadienyl)(cyclopentadienyl)titanium dihydride; (diphenylmethylcyclopentadienyl)(cyclopentadienyl)zirconium dihydride; (ethylcyclopentadienyl)(cyclopentadienyl)hafnium dimethyl; (ethylcyclopentadienyl)(cyclopentadienyl)titanium dimethyl; (ethylcyclopentadienyl)(cyclopentadienyl)zirconium dimethyl; (ethylcyclopentadienyl)(cyclopentadienyl) hafnium dihydride; (ethylcyclopentadienyl)(cyclopentadienyl)titanium dihydride; (ethylcyclopentadienyl) (cyclopentadienyl)zirconium dihydride; (ethyltetramethylcyclopentadienyl) (cyclopentadienyl) hafnium dihydride; (ethyltetramethylcyclopentadienyl)(cyclopentadienyl)hafnium dimethyl; (ethyltetramethylcyclopentadienyl)(cyclopentadienyl)titanium dihydride; (ethyltetramethylcyclopentadienyl)(cyclopentadienyl)titanium dimethyl; (ethyltetramethylcyclopentadienyl)(cyclopentadienyl)zirconium dihydride; (ethyltetramethylcyclopentadienyl)(cyclopentadienyl)zirconium dimethyl; (indenyl)(cyclopentadienyl)hafnium dihydride; (indenyl) (cyclopentadienyl)hafnium dimethyl; (indenyl)(cyclopentadienyl)titanium dihydride; (indenyl)(cyclopentadienyl)titanium dimethyl; (indenyl)(cyclopentadienyl)zirconium dihydride; (indenyl)(cyclopentadienyl)zirconium dimethyl; (methylcyclopentadienyl)(cyclopentadienyl)hafnium dihydride; (methylcyclopentadienyl)(cyclopentadienyl)hafnium dimethyl; (methylcyclopentadienyl) (cyclopentadienyl)titanium dihydride; (methylcyclopentadienyl)(cyclopentadienyl)titanium dimethyl; (methylcyclopentadienyl)(cyclopentadienyl)zirconium dihydride; (methylcyclopentadienyl) (cyclopentadienyl)zirconium dimethyl; (n-butylcyclopentadienyl)(cyclopentadienyl)hafnium dimethyl; (n-butylcyclopentadienyl)(cyclopentadienyl)titanium dimethyl; (n-butylcyclopentadienyl) (cyclopentadienyl)zirconium dimethyl; (n-butylcyclopentadienyl)(cyclopentadienyl)hafnium dihydride; (n-butylcyclopentadienyl)(cyclopentadienyl)titanium dihydride; (n-butylcyclopentadienyl)(cyclopentadienyl)zirconium dihydride; (pentamethylcyclopentadienyl) (cyclopentadienyl)hafnium dihydride; (pentamethylcyclopentadienyl)(cyclopentadienyl)hafnium dimethyl; (pentamethylcyclopentadienyl)(cyclopentadienyl)titanium dihydride; (pentamethylcyclopentadienyl)(cyclopentadienyl)titanium dimethyl; (pentamethylcyclopentadienyl)(cyclopentadienyl)zirconium dihydride; (pentamethylcyclopentadienyl)(cyclopentadienyl)zirconium dimethyl; (propylcyclopentadienyl)(cyclopentadienyl) hafnium dimethyl; (propylcyclopentadienyl)(cyclopentadienyl)titanium dimethyl; (propylcyclopentadienyl)(cyclopentadienyl)zirconium dimethyl; (propylcyclopentadienyl) (cyclopentadienyl)hafnium dihydride; (propylcyclopentadienyl)(cyclopentadienyl)titanium dihydride; (propylcyclopentadienyl)(cyclopentadienyl)zirconium dihydride; (t-butylcyclopentadienyl)(cyclopentadienyl)hafnium dimethyl; (t-butylcyclopentadienyl) (cyclopentadienyl)titanium dimethyl; (t-butylcyclopentadienyl)(cyclopentadienyl)zirconium dimethyl; (t-butylcyclopentadienyl)(cyclopentadienyl)hafnium dihydride; (t-butylcyclopentadienyl)(cyclopentadienyl)titanium dihydride; (t-butylcyclopentadienyl)(cyclopentadienyl)zirconium dihydride; (tetramethylcyclopentadienyl)(cyclopentadienyl)hafnium dihydride; (tetramethylcyclopentadienyl)(cyclopentadienyl)hafnium dimethyl; (tetramethylcyclopentadienyl)(cyclopentadienyl)titanium dihydride; (tetramethylcyclopentadienyl)(cyclopentadienyl) titanium dimethyl; (tetramethylcyclopentadienyl)(cyclopentadienyl)zirconium dihydride; (tetramethylcyclopentadienyl)(cyclopentadienyl)zirconium dimethyl; (trifluoromethylcyclopentadienyl)(cyclopentadienyl) hafnium dihydride; (trifluoromethylcyclopentadienyl)(cyclopentadienyl)titanium dihydride; (trifluoromethylcyclopentadienyl)(cyclopentadienyl)zirconium dihydride; (trifluoromethylcyclopentadienyl)(cyclopentadienyl) hafnium dimethyl; (trifluoromethylcyclopentadienyl)(cyclopentadienyl)titanium dimethyl; (trifluoromethylcyclopentadienyl)(cyclopentadienyl)zirconium dimethyl; (trimethylcyclopentadienyl)(cyclopentadienyl)hafnium dihydride; (trimethylcyclopentadienyl) (cyclopentadienyl) hafnium dimethyl; (trimethylcyclopentadienyl) (cyclopentadienyl)titanium dihydride; (trimethylcyclopentadienyl)(cyclopentadienyl)titanium dimethyl; (trimethylcyclopentadienyl)(cyclopentadienyl)zirconium dihydride; (trimethylcyclopentadienyl)(cyclopentadienyl)zirconium dimethyl; (trimethylgermylcyclopentadienyl)(cyclopentadienyl)hafnium dihydride; (trimethylgermylcyclopentadienyl)(cyclopentadienyl)titanium dihydride; (trimethylgermylcyclopentadienyl) (cyclopentadienyl)zirconium dihydride; (trimethylgermylcyclopentadienyl)(cyclopentadienyl)hafnium dimethyl; (trimethylgermylcyclopentadienyl)(cyclopentadienyl)titanium dimethyl; (trimethylgermylcyclopentadienyl)(cyclopentadienyl)zirconium dimethyl; (trimethylplumbylcyclopentadienyl) (cyclopentadienyl)hafnium dihydride; (trimethylplumbylcyclopentadienyl)(cyclopentadienyl)titanium dihydride; (trimethylplumbylcyclopentadienyl)(cyclopentadienyl)zirconium dihydride; (trimethylplumbylcyclopentadienyl)(cyclopentadienyl)hafnium dimethyl; (trimethylplumbylcyclopentadienyl)(cyclopentadienyl)titanium dimethyl; (trimethylplumnbylcyclopentadienyl)(cyclopentadienyl)zirconium dimethyl; (trimethylsilylcyclopentadienyl)(cyclopentadienyl)hafnium dihydride; (trimethylsilylcyclopentadienyl)(cyclopentadienyl)hafnium dimethyl; (trimethylsilylcyclopentadienyl)(cyclopentadienyl)titanium dihydride; (trimethylsilylcyclopentadienyl)(cyclopentadienyl)titanium dimethyl; (trimethylsilylcyclopentadienyl)(cyclopentadienyl)zirconium dihydride; (trimethylsilylcyclopentadienyl)(cyclopentadienyl)zirconium dimethyl; (trimethylstannylcyclopentadienyl)(cyclopentadienyl) hafnium dihydride; (trimethylstannylcyclopentadienyl)(cyclopentadienyl)titanium dihydride; (trimethylstannylcyclopentadienyl)(cyclopentadienyl)zirconium dihydride; [1,1'-(1,1,2,2-tetramethyldisilanylene)bis(3-methylcyclopentadienyl)]zirconium dimethyl; [1,1'-(1,1,2,2-tetramethyldisilanylene)bis(3-trimethylsilylcyclopentadienyl)]zirconium dimethyl; [1,1'-(1,1,2,2-tetramethyldisilanylene)-bis(4,5,6,7-tetrahydroindenyl)]hafnium dimethyl; [1,1'-(1,1,2,2-tetramethyldisilanylene)-bis(4,5,6,7-tetrahydroindenyl)]titanium dimethyl; [1,1'-(1,1,2,2-tetramethyldisilanylene)-bis(4,5,6,7-tetrahydroindenyl)]zirconium dimethyl; [1,1'-(1,1,3,3-tetramethyldisiloxanylene)bis(4,5,6,7-tetrahydroindenyl)] hafnium dimethyl; [1,1'-(1,1,3,3-tetramethyldisiloxanylene) bis(4,5,6,7-tetrahydroindenyl)]titanium di-methyl; [1,1'-(1,1,3,3-tetramethyldisiloxanylene)bis(4,5,6,7-tetrahydroindenyl)]zirconium dimethyl; [1,1'-(1,1,4,4-tetramethyl-1,4-disilanylbutylene)bis(4,5,6,7-tetrahydroindenyl)]hafnium dimethyl; [1,1'-(1,1,4,4-tetramethyl-1,4-disilanylbutylene)bis(4,5,6,7-tetrahydroindenyl)]titanium dimethyl; [1,1'-(1,1,4,4-tetramethyl-1,4-disilanylbutylene)bis(4,5,6,7-tetrahydroindenyl)]zirconium di-methyl; [1,1'-(2,2-dimethyl-2-silapropylene)-bis(3-methylcyclopentadienyl)] hafnium dimethyl; [1,1'-(2,2-dimethyl-2-silapropylene)-bis (3-methylcyclopentadienyl)]titanium dimethyl; [1,1'-(2,2-dimethyl-2-silapropylene)-bis(3-methylcyclopentadienyl)] zirconium dimethyl; [1,1'-dimethylsilanylenebis(3-methylcyclopentadienyl)]hafnium dimethyl; [1,1'-dimethylsilanylenebis(3-methylcyclopentadienyl)]titanium dimethyl; [1,1'-dimethylsilanylenebis(3-methylcyclopentadienyl)]zirconium dimethyl; [1,1'-dimethylsilanylene-bis(3-trimethylsilanylcyclopentadienyl)]hafnium dimethyl; [1,1'-dimethylsilanylene-bis(3-trimethylsilanylcyclopentadienyl)]titanium dimethyl; [1,1'-dimethylsilanylene-bis(3-trimethylsilanylcyclopentadienyl)]zirconium dimethyl; [1,1'-dimethylsilanylene-bis(4,5,6,7-tetrahydroindenyl)] hafnium dimethyl; [1,1'-dimethylsilanylene-bis(4,5,6,7-tetrahydroindenyl)]titanium dimethyl; [1,1'-dimethylsilanylene-bis(4,5,6,7-tetrahydroindenyl)]zirconium dimethyl; [1,1'-dimethylsilanylene-bis(indenyl)]hafnium dimethyl; [1,1'-dimethylsilanylene-bis(indenyl)]titanium dimethyl; [1,1'-dimethylsilanylenebis(indenyl)]zirconium dimethyl; bis(benzylcyclopentadienyl)hafnium dihydride; bis(benzylcyclopentadienyl)hafnium dimethyl; bis(benzylcyclopentadienyl)titanium dihydride; bis(benzylcyclopentadienyl)titanium dimethyl; bis(benzylcyclopentadienyl)zirconium dihydride; bis(benzylcyclopentadienyl)zirconium dimethyl; bis(cyclohexylmethylcyclopentadienyl)hafnium dihydride; bis(cyclohexylmethylcyclopentadienyl)hafnium dimethyl; bis(cyclohexylmethylcyclopentadienyl)titanium dihydride; bis(cyclohexylmethylcyclopentadienyl)titanium dimethyl; bis(cyclohexylmethylcyclopentadienyl)zirconium dihydride; bis(cyclohexylmethylcyclopentadienyl)zirconium dimethyl; bis(cyclopentadienyl)(trimethylsilyl)(methyl) hafnium; bis(cyclopentadienyl)(trimethylsilyl)(methyl)titanium; bis(cyclopentadienyl)(trimethylsilyl)(methyl)zirconium; bis(cyclopentadienyl)[tris(dimethylsilyl)silyl] (methyl)hafnium; bis(cyclopentadienyl)[tris(dimethylsilyl)silyl](methyl)titanium; bis(cyclopentadienyl)[tris (dimethylsilyl)silyl](methyl)zirconium; bis (cyclopentadienyl)(trimethylsilyl)(tris(trimethylsilyl) (trimethylsilylbenzyl); bis(cyclopentadienyl)(triphenylsilyl) (methyl)hafnium; bis(cyclopentadienyl)(triphenylsilyl) (methyl)titanium; bis(cyclopentadienyl)(triphenylsilyl) (methyl)zirconium; bis(cyclopentadienyl)hafnium di(m-tolyl); bis(cyclopentadienyl)hafnium di(p-tolyl); bis (cyclopentadienyl)hafnium dibutyl; bis(cyclopentadienyl) hafnium diethyl; bis(cyclopentadienyl)hafnium dihydride; bis(cyclopentadienyl)hafnium dimethyl; bis(cyclopentadienyl)hafnium dineopentyl; bis(cyclopentadienyl)hafnium diphenyl; bis(cyclopentadienyl)hafnium dipropyl; bis(cyclopentadienyl)titanium di(m-tolyl); bis(cyclopentadienyl) titanium di(p-tolyl); bis(cyclopentadienyl)titanium dibutyl; bis(cyclopentadienyl)titanium diethyl; bis(cyclopentadienyl)titanium dihydride; bis(cyclopentadienyl)titanium dimethyl; bis(cyclopentadienyl)titanium dineopentyl; bis(cyclopentadienyl)titanium diphenyl; bis(cyclopentadienyl) titanium dipropyl; bis(cyclopentadienyl)zirconium di(m-tolyl); bis(cyclopentadienyl)zirconium di(p-tolyl); bis (cyclopentadienyl)zirconium dibutyl; bis(cyclopentadienyl) zirconium diethyl; bis(cyclopentadienyl)zirconium dihydride; bis(cyclopentadienyl)zirconium dimethyl; bis (cyclopentadienyl)zirconium dineopentyl; bis(cyclopentadienyl)zirconium diphenyl; bis(cyclopentadienyl)zirconium dipropyl; bis(dimethylcyclopentadienyl)hafnium dihydride; bis(dimethylcyclopentadienyl)hafnium dimethyl; bis(dimethylcyclopentadienyl)titanium dihydride; bis(dimethylcyclopentadienyl)titanium dimethyl; bis(dimethylcyclopentadienyl)zirconium dihydride; bis(dimethylcyclopentadienyl)zirconium dimethyl; bis(diphenylmethylcyclopentadienyl)hafnium dihydride; bis(diphenylmethylcyclopentadienyl)hafnium dimethyl; bis(diphenylmethylcyclopentadienyl)titanium dihydride; bis(diphenylmethylcyclopentadienyl)titanium dimethyl; bis(diphenylmethylcyclopentadienyl)zirconium dihydride; bis(diphenylmethylcyclopentadienyl)zirconium dimethyl; bis(ethylcyclopentadienyl)hafnium dimethyl; bis(ethylcyclopentadienyl)titanium dimethyl; bis(ethylcyclopentadienyl)zirconium dimethyl; bis(ethyltetramethylcyclopentadienyl)hafnium dimethyl; bis(ethyltetramethylcyclopentadienyl)titanium dimethyl; bis(ethyltetramethylcyclopentadienyl)zirconium dimethyl; bis(ethyltetramethylcyclopentadienyl)hafnium dihydride; bis(ethyltetramethylcyclopentadienyl)titanium dihydride; bis(ethyltetramethylcyclopentadienyl)zirconium dihydride; bis(indenyl)hafnium dihydride; bis(indenyl)hafnium dimethyl; bis(indenyl)titanium dihydride; bis(indenyl)titanium dimethyl; bis(indenyl)zirconium dihydride; bis(indenyl)zirconium dimethyl, bis(methylcyclopentadienyl)hafnium dimethyl; bis(methylcyclopentadienyl)titanium dimethyl; bis(methylcyclopentadienyl)zirconium dimethyl; bis(methylcyclopentadienyl)hafnium dihydride; bis(methylcyclopentadienyl)titanium dihydride; bis(methylcyclopentadienyl)zirconium dihydride; bis(n-butylcyclopentadienyl)hafnium dimethyl; bis(n-butylcyclopentadienyl)titanium dimethyl; bis(n-butylcyclopentadienyl)zirconium dimethyl; bis(n-butylcyclopentadienyl)hafnium dihydride; bis(n-butylcyclopentadienyl)titanium dihydride; bis(n-butylcyclopentadienyl)zirconium dihydride; bis(pentamethylcyclopentadienyl)(benzyne)hafnium; bis(pentamethylcyclopentadienyl)(benzyne)titanium; bis(pentamethylcyclopentadienyl)(benzyne)zirconium; bis(pentamethylcyclopentadienyl)hafnium dimethyl; bis(pentamethylcyclopentadienyl)titanium dimethyl; bis(pentamethylcyclopentadienyl)zirconacyclopentane; bis(pentamethylcyclopentadienyl)zirconium dimethyl; bis(pentamethylcyclopentadienyl)hafnium (methyl)(hydride); bis(pentamethylcyclopentadienyl)hafnium (phenyl)(hydride); bis(pentamethylcyclopentadienyl)hafnium dihydride; bis(pentamethylcyclopentadienyl)titanium (methyl)(hydride); bis(pentamethylcyclopentadienyl)titanium (phenyl)(hydride); bis(pentamethylcyclopentadienyl)titanium dihydride; bis(pentamethylcyclopentadienyl)zirconacyclobutane; bis(pentamethylcyclopentadienyl)zirconium (methyl)(hydride); bis(pentamethylcyclopentadienyl)zirconium (phenyl)(hydride); bis(pentamethylcyclopentadienyl)zirconium dihydride; bis(propylcyclopentadienyl)hafnium dimethyl; bis(propylcyclopentadienyl)titanium dimethyl; bis(propylcyclopentadienyl)zirconium dimethyl; bis(propylcyclopentadienyl)hafnium dihydride; bis(propylcyclopentadienyl)titanium dihydride; bis(propylcyclopentadienyl)zirconium dihydride; bis(t-butylcyclopentadienyl)hafnium dimethyl; bis(t-butylcyclopentadienyl)titanium dimethyl; bis(t-butylcyclopentadienyl)zirconium dimethyl; bis(t-butylcyclopentadienyl)hafnium dihydride; bis(t-butylcyclopentadienyl)titanium dihydride; bis(t-butylcyclopentadienyl)zirconium dihydride; bis(tetramethylcyclopentadienyl)hafnium dihydride; bis(tetramethylcyclopentadienyl)hafnium dimethyl; bis(tetramethylcyclopentadienyl)titanium dihydride; bis(tetramethylcyclopentadienyl)titanium dimethyl; bis(tetramethylcyclopentadienyl)zirconium dihydride; bis(tetramethylcyclopentadienyl)zirconium dimethyl; bis(trifluoromethylcyclopentadienyl)hafnium dihydride; bis(trifluoromethylcyclopentadienyl)hafnium dimethyl; bis(trifluoromethylcyclopentadienyl)titanium dihydride; bis(trifluoromethylcyclopentadienyl)titanium dimethyl; bis(trifluoromethylcyclopentadienyl)zirconium dihydride; bis(trifluoromethylcyclopentadienyl)zirconium dimethyl; bis(trimethylcyclopentadienyl)hafnium dihydride; bis(trimethylcyclopentadienyl)hafnium dimethyl; bis(trimethylcyclopentadienyl)titanium dihydride; bis(trimethylcyclopentadienyl)titanium dimethyl; bis(trimethylcyclopentadienyl)zirconium dihydride; bis(trimethylcyclopentadienyl)zirconium dimethyl; bis(trimethylgermylcyclopentadienyl)hafnium dihydride; bis(trimethylgermylcyclopentadienyl)hafnium dimethyl; bis(trimethylgermylcyclopentadienyl)titanium dihydride; bis(trimethylgermylcyclopentadienyl)titanium dimethyl; bis(trimethylgermylcyclopentadienyl)zirconium dihydride; bis(trimethylgermylcyclopentadienyl)zirconium dimethyl; bis(trimethylplumbylcyclopentadienyl)hafnium dihydride; bis(trimethylplumbylcyclopentadienyl)hafnium dimethyl; bis(trimethylplumbylcyclopentadienyl)titanium dihydride; bis(trimethylplumbylcyclopentadienyl)titanium dimethyl; bis(trimethylplumbylcyclopentadienyl)zirconium dihydride; bis(trimethylplumbylcyclopentadienyl)zirconium dimethyl; bis(trimethylsilylcyclopentadienyl)hafnium dihydride; bis(trimethylsilylcyclopentadienyl)hafnium dimethyl; bis(trimethylsilylcyclopentadienyl)titanium dihydride; bis(trimethylsilylcyclopentadienyl)titanium dimethyl; bis(trimethylsilylcyclopentadienyl)zirconium dihydride; bis(trimethylsilylcyclopentadienyl)zirconium dimethyl; bis(trimethylstannylcyclopentadienyl)hafnium dihydride; bis(trimethylstannylcyclopentadienyl)titanium dihydride; bis(trimethylstannylcyclopentadienyl)zirconium dihydride; dibutylsilyl (fluorenyl) (cyclopentadienyl)hafnium dimethyl; diethylsilanediylbis-(2-methylindenyl)-zirconium diethyl,; diethylsilanediylbis-(2-methylindenyl)-zirconium dimethyl,; dimethylsilanediylbis-(2-ethyl-5-isopropylcyclopentadienyl)-zirconium dimethyl,; dimethylsilanediylbis-(2-ethylindenyl)-zirconium dimethyl,; dimethylsilanediyl-bis-(2-isopropylindenyl)-zirconium dimethyl,; dimethylsilanediylbis-(2-methyl-5-ethylcyclopentadienyl)-zirconium dimethyl,; dimethylsilanediylbis-(2-methyl-5-methylcyclopentadienyl)-zirconium dimethyl,; dimethylsilanediylbis-(2-methylbenzindenyl)-zirconium dimethyl; dimethylsilanediylbis-(2-methylindanyl)-zirconium dimethyl,; dimethylsilanediylbis-(2-methylindenyl)-hafnium dimethyl.; dimethylsilanediylbis-(2-methylindenyl)-zirconium dimethyl,; dimethylsilanediylbis-(2-tert-butylindenyl)-zirconium dimethyl,; dimethylsilyl (indenyl)(fluorenyl) hafnium dihydride; dimethylsilyl bis(2-methyl-indenyl) hafnium dimethyl; dimethylsilyl bis(2-propyl-indenyl) hafnium dimethyl; dimethylsilyl bis(4-methyl, 2-phenyl-indenyl)hafnium dimethyl; dimethylsilyl bis(cyclopentadienyl)hafnium dihydride; dimethylsilyl bis(cyclopentadienyl)titanium dihydride; dimethylsilyl bis(cyclopentadienyl)zirconium dihydride; dimethylsilyl bis(indenyl)hafnium dimethyl; dimethylsilyl (methylcyclopentadienyl)(1-fluorenyl)hafnium dihydride; dimethylsilyl(methylcyclopentadienyl)(1-fluorenyl)titanium dihydride; dimethylsilyl(methylcyclopentadienyl)(1-fluorenyl)zirconium dihydride; dimethylsilylbis(3-trimethylsilylcyclopentadienyl)hafnium dihydride; dimethylsilylbis(3-trimethylsilylcyclopentadienyl)titanium dihydride; dimethylsilylbis(3-trimethylsilylcyclopentadienyl)zirconium dihydride; dimethylsilylbis(indenyl)hafnium dimethyl; dimethylsilylbis(indenyl)titanium dimethyl; dimethylsilylbis(indenyl)zirconium dimethyl; dimethylthiobis-(2-methylindenyl)-zirconium dimethyl,; dinapthylmethylene (cyclopentadienyl)(fluorenyl)hafnium dimethyl; diphenylmethylene (2,7-di-n-butyl fluorenyl)(cyclopentadienyl) hafnium dimethyl; diphenylmethylene (2,7-di-n-butyl fluorenyl)(fluorenyl)hafnium dimethyl; diphenylmethylene (2,7-di-t-butyl fluorenyl)(cyclopentadienyl)hafnium dimethyl; diphenylmethylene (2,7-di-t-butyl fluorenyl)(fluorenyl)hafnium dimethyl; diphenylmethylene (2,7-di-t-butyl-5-methylfluorenyl)(cyclopentadienyl)hafnium dimethyl; diphenylmethylene (cyclopentadienyl)(2,7-dimethyl fluorenyl)hafnium dimethyl; diphenylmethylene (cyclopentadienyl)(2,7-di-t-butyl fluorenyl)hafnium dimethyl; diphenylmethylene (indenyl)(2,7-di-t-butyl fluorenyl)hafnium dibenzyl; ethylene bis(cyclopentadienyl)hafnium dihydride; ethylene bis(cyclopentadienyl)hafnium dihydride; dimethylsilyl bis(cyclopentadienyl)hafnium dihydride; ethylene bis(cyclopentadienyl)hafnium dimethyl; ethylene bis(cyclopentadienyl)titanium dihydride; ethylene bis(cyclopentadienyl)titanium dihydride; dimethylsilyl bis(cyclopentadienyl)titanium dihydride; ethylene bis(cyclopentadienyl)titanium dimethyl; ethylene bis(cyclopentadienyl)zirconium dihydride; ethylene bis(cyclopentadienyl)zirconium dihydride; ethylene bis(cyclopentadienyl)zirconium dimethyl; ethylenebis(indenyl)hafnium dimethyl; ethylenebis(indenyl)titanium dimethyl; ethylenebis(indenyl)zirconium dimethyl; ethylenebis(tetrahydroindenyl)hafnium dimethyl; ethylenebis(tetrahydroindenyl)titanium dimethyl; ethylenebis(tetrahydroindenyl)zirconium dimethyl; i-propyl (cyclopentadienyl)(fluorenyl)hafnium dimethyl; isopropyl(cyclopentadienyl)(1-fluorenyl)hafnium dimethyl; isopropyl(cyclopentadienyl)(1-fluorenyl)titanium dimethyl; isopropyl(cyclopentadienyl)(1-fluorenyl)zirconium dimethyl; isopropyl(cyclopentadienyl)(1-octahydro-fluorenyl)hafnium dimethyl; isopropyl(cyclopentadienyl)(1-octahydro-fluorenyl)titanium dimethyl; isopropyl(cyclopentadienyl)(1-octahydro-fluorenyl)zirconium dimethyl; methylene (2,7-di-t-butyl fluorenyl)(fluorenyl)hafnium dimethyl; methylene (indenyl)(2,7-di-t-butyl-fluorenyl)hafnium dimethyl; methylene bis(cyclopentadienyl)hafnium dimethyl; methylene bis(cyclopentadienyl)titanium dimethyl; methylene bis(cyclopentadienyl)zirconium dimethyl; methylene bis(fluorenyl)hafnium dimethyl; methylene(cyclopetadienyl (tetramethylcyclopentadienyl)hafnium dimethyl; methylene (cyclopentadienyl (tetramethylcyclopentadienyl)titanium dimethyl; methylene(cyclopentadienyl (tetramethylcyclopentadienyl)zirconium dimethyl; methylene(cyclopentadienyl)(1-fluorenyl)hafnium dihydride; methylene(cyclopentadienyl)(1-fluorenyl)titanium dihydride; methylene (cyclopentadienyl)(1-fluorenyl)zirconium dihydride; methylphenylmethylene bis(fluorenyl)hafnium dimethyl; bis(methylcyclopentadienyl)zirconium dimethyl; bis(ethylcyclopentadienyl)zirconium dimethyl; bis(methylcyclopentadienyl)zirconium dimethyl; bis(ethylcyclopentadienyl)zirconium dimethyl; bis(methylcyclopentadienyl)zirconium dihydride; bis(ethylcyclopentadienyl)zirconium dihydride; bis(dimethylcyclopentadienyl)zirconium dimethyl; bis(trimethylcyclopentadienyl)zirconium dimethyl; bis(tetramethylcyclopentadienyl)zirconium dimethyl; bis(ethyltetramethylcyclopentadienyl)zirconium dimethyl; bis(indenyl)zirconium dimethyl; bis(dimethylcyclopentadienyl)zirconium dimethyl; bis(trimethylcyclopentadienyl)zirconium dimethyl; bis(tetramethylcyclopentadienyl)zirconium dimethyl; bis(ethyltetramethylcyclopentadienyl)zirconium dimethyl; bis(indenyl)zirconium dimethyl; bis(dimethylcyclopentadienyl)zirconium dihydride; bis(trimethylcyclopentadienyl)zirconium dihydride; bis(ethyltetramethylcyclopentadienyl)zirconium dihydride; bis(trimethylsilylcyclopentadienyl)zirconium dimethyl; bis(trimethylsilylcyclopentadienyl)zirconium dihydride; bis(trifluoromethylcyclopentadienyl)zirconium dimethyl; bis(trifluoromethylcyclopentadienyl)zirconium dimethyl; bis(trifluoromethylcyclopentadienyl)zirconium dihydride; isopropylidenebis(indenyl)zirconium dimethyl; isopropylidene-bis(indenyl)zirconium dimethyl; isopropylidene-bis(indenyl)zirconium dihydride; pentamethylcyclopentadienyl(cyclopentadienyl)zirconium dimethyl; pentamethylcyclopentadienyl(cyclopentadienyl)zirconium dimethyl; pentamethylcyclopentadienyl(cyclopentadienyl)zirconium dihydride; ethyltetramethylcyclopentadienyl(cyclopentadienyl)zirconium dihydride; isopropylidene(cyclopentadienyl)(fluorenyl)zirconium dimethyl; isopropylidene(cyclopentadienyl)(fluorenyl)zirconium dimethyl; dimethylsilyl(cyclopentadienyl)(fluorenyl)zirconium dimethyl; isopropylidene(cyclopentadienyl)(fluorenyl)zirconium dihydride, bis(cyclopentadienyl)zirconium dimethyl; bis(cyclopentadienyl)zirconium dimethyl; bis(cyclopentadienyl)zirconium diethyl; bis(cyclopentadienyl)zirconium dipropyl; bis(cyclopentadienyl)zirconium diphenyl; methylcyclopentadienyl(cyclopentadienyl)zirconium dimethyl; ethylcyclopentadienyl(cyclopentadienyl)zirconium dimethyl; methylcyclopentadienyl(cyclopentadienyl)zirconium dimethyl; ethylcyclopentadienyl(cyclopentadienyl)zirconium dimethyl; methylcyclopentadienyl(cyclopentadienyl)zirconium dihydride; ethylcyclopentadienyl(cyclopentadienyl)zirconium dihydride; dimethylcyclopentadienyl(cyclopentadienyl)zirconium dimethyl; trimethylcyclopentadienyl(cyclopentadienyl)zirconium dimethyl; tetramethylcyclopentadienyl(cyclopentadienyl)zirconium dimethyl; bis(pentamethylcyclopentadienyl)zirconium dimethyl; tetramethylcyclopentadienyl(cyclopentadienyl)zirconium dimethyl; indenyl(cyclopentadienyl)zirconium dimethyl; dimethylcyclopentadienyl(cyclopentadienyl)zirconium dimethyl; trimethylcyclopentadienyl(cyclopentadienyl)zirconium dimethyl; tetramethylcyclopentadienyl(cyclopentadienyl)zirconium dimethyl; bis(pentamethylcyclopentadienyl)zirconium dimethyl; ethyltetramethylcyclopentadienyl(cyclopentadienyl)zirconium dimethyl; indenyl(cyclopentadienyl)zirconium dimethyl; dimethylcyclopentadienyl(cyclopentadienyl)zirconium dihydride; trimethylcyclopentadienyl(cyclopentadienyl)zirconium dihydride; bis(pentamethylcyclopentadienyl)zirconium dihydride; indenyl(cyclopentadienyl)zirconium dihydride; trimethylsilylcyclopentadienyl(cyclopentadienyl)zirconium dimethyl; trimethylsilylcyclopentadienyl(cyclopentadienyl)zirconium dihydride; trifluoromethylcyclopentadienyl(cyclopentadienyl)zirconium dimethyl; trifluoromethylcyclopentadienyl(cyclopentadienyl)zirconium dimethyl; trifluoromethylcyclopentadienyl(cyclopentadienyl)zirconium dihydride; bis(cyclopentadienyl)(trimethylsilyl)(methyl)zirconium; bis(cyclopentadienyl)(triphenylsilyl)(methyl)zirconium; bis(cyclopentadienyl)[tris(dimethylsilyl)silyl](methyl)zirconium; bis(cyclopentadienyl)[bis(methylsilyl)silyl](methyl)zirconium; bis(cyclopentadienyl)(trimethylsilyl)(trimethylsilyl methyl)zirconium; bis(cyclopentadienyl)(trimethylsilyl)(benzyl)zirconium; methylenebis(cyclopentadienyl)zirconium dimethyl; ethylenebis(cyclopentadienyl)zirconium dimethyl; isopropylidenebis(cyclopentadienyl)zirconium dimethyl; dimethylsilylbis(cyclopentadienyl)zirconium dimethyl; methylenebis(cyclopentadienyl)zirconium dimethyl; ethylenebis(cyclopentadienyl)zirconium dimethyl; ethylenebis (cyclopentadienyl)zirconium dimethyl; isopropylidenebis (cyclopentadienyl)zirconium dimethyl; dimethylsilylbis (cyclopentadienyl)zirconium dimethyl; methylenebis (cyclopentadienyl)zirconium dihydride; ethylenebis (cyclopentadienyl)zirconium dihydride; isopropylidenebis (cyclopentadienyl)zirconium dihydride; dimethylsilylbis (cyclopentadienyl)zirconium dihydride.; (Pentamethylcyclopentadienyl)zirconium trimethyl; (Pentamethylcyclopentadienyl)zirconium triphenyl; (Pentamethylcyclopentadienyl)zirconium tribenzyl; (Pentamethylcyclopentadienyl)zirconium trimethyl; (Cyclopentadienyl) zirconium trimethyl; (Cyclopentadienyl)zirconium triphenyl; (Cyclopentadienyl)zirconium tribenzyl; (Cyclopentadienyl)zirconium trimethyl; (ethylcyclopentadienyl) zirconium trimethyl; (Methylcyclopentadienyl)zirconium triphenyl; (Methylcyclopentadienyl)zirconium tribenzyl; (Methylcyclopentadienyl)zirconium trimethyl; (Dimethylcyclopentadienyl)zirconium trimethyl; (Trimethylcyclopentadienyl)zirconium trimethyl; (Trimethylsilylcyclopentadienyl)zirconium trimethyl; (Tetramethylcyclopentadienyl) zirconium trimethyl; Indenylzirconium trimethyl; Fluorenylzirconium trimethyl; Bis(cyclopentadienyl)zirconium dimethyl; Bis(cyclopentadienl)zirconium diphenyl; Bis(cyclopentadienyl)zirconium dibenzyl; Bis(cyclopentadienyl)zirconium dimethyl; Bis(cyclopentadienyl)zirconium diethyl; Bis(cyclopentadienyl)zirconium dihydride; Bis(cyclopentadienyl)zirconium dichlorohydride; Bis(methylcyclopentadienyl)zirconium dimethyl; Bis(methylcyclopentadienyl)zirconium diphenyl; Bis(methylcyclopentadienyl)zirconium dibenzyl; Bis(methylcyclopentadienyl) zirconium dimethyl; Bis(pentamethylcyclopentadienyl) zirconium dimethyl; Bis(pentamethylcyclopentadienyl) zirconium dimethyl; Bis(pentamethylcyclopentadienyl) zirconium dibenzyl; Bis(pentamethylcyclopentadienyl) zirconium methylmethyl; Bis (pentamethylcyclopentadienyl)zirconium methylhydride; Ethylenebis(indenyl)zirconium dimethyl; Ethylenebis(indenyl)zirconium dimethyl; Ethylenebis(tetrahydroindenyl)zirconium dimethyl; Ethylenebis(tetrahydroindenyl)zirconium dimethyl; Dimethylsilylenebis(cyclopentadienyl)zirconium dimethyl; Dimethylsilylenebis(cyclopentadienyl)zirconium dimethyl; Isopropylidene(cyclopentadienyl)(9fluorenyl)zirconium dimethyl; Phenylmethylmethylene(cyclopentadienyl)(9-fluorenyl)zirconium dimethyl; Diphenylmethylene (cyclopentadienyl)(9-fluorenyl)zirconium dimethyl; Ethylene(cyclopentadienyl)(9-fluorenyl)zirconium dimethyl; Cyclohyxylidene(cyclopentadienyl)(9-fluorenyl)zirconium dimethyl; Cyclopentylidene(cyclopentadienyl)(9-fluorenyl)zirconium dimethyl; Cyclobutylidene (cyclopentadienyl)(9-fluorenyl)zirconium dimethyl; Dimethylsilylene(cyclopentadienyl)(9-fluorenyl)zirconium dimethyl; Dimethylsilylenebis(2,3,5-trim ethylcyclopentadienyl)zirconium dimethyl; Dimethylsilylenebis(2,3,5-trimethylcyclopentadienyl)zirconium dimethyl; Dimethylsilylenebis(indenyl)zirconium dimethyl; Zirconium tetramethyl; Zirconium tetrabenzyl; Zirconium tetramethyl; Zirconium tetramethyl; Zirconium butoxytrimethyl; Zirconium dibutoxydimethyl; Bis(2,5-di-t-butylphenoxy)zirconium dimethyl; Bis(2,5-di-t-butylphenoxy)zirconium dimethyl; Zirconium bis(acetylacetonate)dimethyl; dimethylsilyl (tetramethylcyclopentadienyl)cycldodecyloamido)titanium dimethyl; dimethylsilyl(tetra-methyleyclo-pentadienyl)(1-adamantylamido)titanium dimethyl; dimethylsilyl(tetramethylcyclopentadienyl)(t-butylamido)titanium dimethyl; cyclopentadienylzirconium trimethyl; cyclopentadienylzirconium triethyl; cyclopentadienylzirconium tripropyl; cyclopentadienyltitanium trimethyl; cyclopentadienyltitanium triphenyl; cyclopentadienylscandium bis(p-tolyl); cyclopentadienylchromium 2,4-pentadienyl; (pentamethylcyclopentadienyl)yttrium bis(bistrimethylsilylmethyl); (pentamethylcyclopentadienyl)scandium bis(bistrimethylsilylmethyl); pentamethylcyclopentadienyl lanthanum bis (bistrimethyl-silylmethyl); [1,1'-dimethylsilanylene-bis(2-methyl-indenyl)]hafnium dimethyl; [1,1'-dimethylsilanylene-bis(2-methyl-4-phenyl-lindenyl)] hafnium dimethyl; [1,1'-dimethylsilanylene-bis(2-methy4-naphthyl-2-yl-lindenyl)]hafnium dimethyl; diphenylmethylene (cyclopentadienyl)(fluorenyl)hafnium dimethyl; [(4-n-butylphenyl)(4-t-butylphenyl)methylene] (cyclopentadienyl)(fluorenyl)hafnium dimethyl; dimethylsilanylene (tetramethylcyclopentadienyl)(N-adamantylamido) titanium dimethyl; dimethylsilanylene (tetramethylcyclopentadienyl)(N-t-butylamido)titanium dimethyl; bis(4-[triethylsilyl])methylene (cyclopentadienyl) (fluorenyl)hafnium dimethyl; bis(4-[triethylsilyl])methylene (cyclopentadienyl) (2,7-di-t-butylfluorenyl)hafnium dimethyl;

The following non-metallocene olefin polymerization catalysts are activable by invention partially fluorinated discrete activators:

bis(di-trimethylsilylamido)zirconium dibenzyl; bis(ditrimethylsilylamido)hafnium dibenzyl; bis(di-trimethylsilylamido)titanium dibenzyl; bis(di-trimethylsilylamido)zirconium dimethyl; bis(ditrimethylsilylamido)hafnium dimethyl; bis(di-trimethylsilylamido)titanium dimethyl; bis (di-isobutylamido)hafnium dimethyl; bis(di-tertbutylamido) zirconium dimethyl; (di-cyclohexylamido)(di-trimethylsilylamido)titanium dihydride; tris(di-trimethylsilylamido) zirconium methyl; tris(di-triphenylgermylamido)hafnium methyl; bis(di-trimethylsilylamido)zirconium dimethyl; bis (ditrimethylsilylamido)hafnium dimethyl; bis(di-trimethylsilylamido)titanium dimethyl; bis(di-phenylsilylamido)zirconium dimethyl; bis(di-trimethylsilylamido) hafnium dimethyl; bis(di-trimethylsilylamido)titanium dimethyl.

EXAMPLES

The following examples are presented to illustrate the foregoing discussion. All parts, proportions, and percentages are by weight unless otherwise indicated. The examples are directed to particular invention embodiments; they do not limit the invention in any specific respect.

Preparation of $BrC_{10}H_3F_4$: The preparation of $BrC_{10}H_3F_4$ was as described in *Journal of the Chemical Society* (C)1971, pp. 604.

Synthesis of $[Li(Et_2O)2.5][B(C_{10}H_3F_4)_4]$: Butyl lithium in hexanes (4.2 milliliters, 1.6M, Aldrich)was added to a cold (−78° C., acetone/dry ice bath)diethylether solution of $BrC_{10}H_3F_4$ (1.870 grams). The reaction mixture was stirred for 30 minutes. Boron trichloride (1.67 milliliter, 1.0M, Aldrich)was added to the reaction, after which the cold bath was removed. The reaction was allowed to reach room temperature. Afterwards, the ether was replaced with methylene chloride, and the product was extracted by filtration. The solvent was removed, and the product triturated with pentane. (yellow crystalline solid, 1.422 grams, 82%) $^{19}F$ NMR (CD2Cl2, 25 C): −153.8 (q, 8F), −164.5 (t, 4F), −165.8 (t, 4F).

Synthesis of $[4-tBu-C_6H_4NMe_2H][B(C_{10}H_3F_4)_4]$: 4-tBu-$C_6H_4$ $NMe_2HCl$ (0.293 grams)was added to a methylene chloride solution of $[Li(Et_2O)_{2.5}][B(C_{10}H_3F_4)_4]$(1.422 grams). The mixture was stirred for 1 hour. Lithium chloride precipitated and was collected by filtration. The filtrate was triturated and washed with pentane yielding a white crystalline solid. This solid was characterized by NMR spectroscopy.

Polymerization: Polymerizations using dimethylsilylbis(indenyl)hafnium dimethyl as the polymerization catalyst were carried out in a 1-liter stirred reactor with continuous reactant feed and continuous product withdrawal. The solvent was hexane. Ethylene and propylene were purified over alumina and molecular sieve beds. Toluene for preparing catalyst solutions was also purified using this technique. Metering pumps were used for all feeds except for ethylene, which as a gas flowed under its own pressure through a mass-flow controller. Reactor temperature was controlled in these examples by circulating water through a reactor cooling jacket. The reactors were maintained pressurized to above the reactant-mixture vapor pressure to keep the reactants liquefied. The reactors were operated liquid-full. Residence time was set by reactor volumes and flow rates. Residence time, defined as the average time reactants spend within the reactor was 5-50 minutes.

Ethylene and propylene feeds were combined into one stream and then mixed with a 0° C., pre-chilled hexane stream. Polymer composition was controlled by the relative monomer(s)amount fed to the reactor. Enough hexane tri-n-octyl aluminum scavenger solution was added to the combined solvent and monomer stream, just before the feed entered the reactor, to further reduce the catalyst poison concentration. Catalyst components mixed in toluene were separately pumped to the reactor and injected through a separate port.

Product exited through a pressure control valve that reduced the pressure to atmospheric. This caused dissolved, unconverted monomer to flash into a gas, which was vented from the top of a vapor-liquid separator. The liquid, comprising mainly polymer and solvent, flowed out of the separator bottom and was collected for the polymer solution. Invention polymers were recovered by steam stripping followed by drying, or by precipitating them with a polar solvent such as acetone, followed by residual solvent evaporation under heat and vacuum.

Polymer product was characterized by Mooney viscosity (Mooney Viscometer, ASTM D-1648), ethylene content (by FTIR, ASTM D-3900), melt or glass transition temperature (by Differential Scanning Calorimetry (DSC)), and molecular weight (by Gel Permeation Chromatography (GPC)). GPC, as used to characterize invention products, has been described in several publications, notably U.S. Pat. No. 4,989,436. Molecular weight and composition measurements are described in G. Ver Strate, C. Cozewith, S. Ju, *Macromolecules*, 21, 3360 (1988). DSC was used to characterize invention products using a standard protocol of loading the calorimeter at 20° C. with a specimen free of molding strains, annealing at room temperature for 40 hours, cooling the sample to −75° C., scanning to 180° C. at 10° C./min., cooling to −75° C., and re-running the scan. $T_g$, $T_m$, and heat of fusion were evaluated. In some cases, low melting crystallinity was not seen on the second scan as it may take many hours to develop even at low temperatures. Polymer molecular weight is controlled by reactor temperature, monomer concentration, and by the addition of chain transfer agents such as hydrogen.

Polymer solution samples were analyzed for polymer concentration. From this measurement and the reactor feed rates, polymerization rates could be determined using material balances. Monomer conversions were then calculated from the rate and composition data A polymerization series was carried out to demonstrate invention products and processes. Table 1 shows reactor conditions, polymer analyses. Table 2 shows polymerization results.

TABLE 1

| Catalyst[a] | Activator[b] | Product collection | | | | | | Monomer | | | |
| | | Wt. g | Conc., % | Time, min | poly rate, g/hr | % C2 in | | Temp, °C. | Feeds, g/hr | | cat feed, g/hr | Res time, min |
| | | | | | | EP | ML | | C2= | C4= | | |
| W | I | 1232 | 9.0 | 20 | 331.5 | 12.6 | 7.3 | 80 | 53.7 | 811.5 | 0.00747 | 9.36 |
| W | I | 1253.2 | 6.9 | 20 | 260.2 | 13.4 | 10.8 | 80 | 53.7 | 811.5 | 0.0042 | 9.07 |
| W | II | 1508.7 | 14.0 | 20 | 634.6 | 12.8 | 2.8 | 60 | 75 | 811.5 | 0.014 | 8.29 |
| W | II | 1496.1 | 13.3 | 20 | 596.9 | 11.5 | 3.3 | 60 | 75 | 811.5 | 0.01073 | 8.29 |
| W | II | 1447 | 11.3 | 20 | 488.8 | 12.3 | 5.4 | 60 | 75 | 811.5 | 0.00747 | 8.36 |
| W | II | 1267.4 | 10.2 | 20 | 387.1 | 14.6 | 9.8 | 60 | 75 | 811.5 | 0.0042 | 9.21 |

[a] W is dimethylsilylbis(indenyl)hafnium dimethyl
[b] I is [4-tBu-$C_6H_4$N$(CH_3)_2$H][B$(C_{10}H_3F_4)_4$] II is [$C_6H_5$N$(CH_3)_2$H][B$(C_6F_5)_4$]

TABLE 2

| catalyst precursor[a] | Activator[b] | Monomer Conv., % | | Catalyst Efficiency | | cat | Scav/Cat | C3/C6 ratio | Mw, Lalls |
| | | C2= | C3= | (g/g) | Kg/mole | (mol/hr) | (mol/mol) | | |
| W | I | 77.7 | 35.7 | 44382 | 21969 | 1.51E−05 | 20.9 | 15% | |
| W | I | 64.8 | 27.8 | 61944 | 30663 | 8.48E−06 | 37.3 | 16% | |
| W | II | 108.6 | 68.2 | 45326 | 22437 | 2.83E−05 | 11.2 | 7% | 129629 |
| W | II | 91.8 | 65.1 | 55633 | 27539 | 2.17E−05 | 14.6 | 8% | 134533 |
| W | II | 80.2 | 52.8 | 65435 | 32391 | 1.51E−05 | 20.9 | 11% | 153071 |
| W | II | 75.5 | 40.7 | 92158 | 45619 | 8.48E−06 | 37.3 | 13% | 176126 |

[a] W is dimethylsilylbis(indenyl)hafnium dimethyl
[b] I is [4-tBu-$C_6H_4$N$(CH_3)_2$H][B$(C_{10}H_3F_4)_4$] II is [$C_6H_5$N$(CH_3)_2$H][B$(C_6F_5)_4$]

While certain representative embodiments and details have been shown to illustrate the invention, it will be apparent to skilled artisans that various process and product changes from those disclosed in this application may be made without departing from this invention's scope, which the appended claims define.

All cited patents, test procedures, priority documents, and other cited documents are fully incorporated by reference to the extent that this material is consistent with this specification and for all jurisdictions in which such incorporation is permitted.

Certain features of the present invention are described in terms of a set of numerical upper limits and a set of numerical lower limits. This specification discloses all ranges formed by any combination of these limits. All combinations of these limits are within the scope of the invention unless otherwise indicated.

We claim:

1. An activator comprising an anionic or neutral central core comprising at least one Group-13 atom connected to three or four fused-ring assemblies, wherein the fused ring assemblies comprise:

a first aromatic ring that is perhydridosubstituted; and
a second aromatic ring that is perfluorosubstituted,
wherein at least one fused-ring assembly is a naphthyl-based radical.

2. The activator of claim 1 wherein each fused-ring assembly is a naphthyl-based radical.

3. The activator of claim 1 wherein the Group-13 atom is boron.

4. The activator of claim 1 wherein the activator is tris(5,6,7,8-tetrafluoro)napth-2-yl borane.

5. The activator of claim 1 comprising four fused-ring assemblies and a cation, wherein the cation is one selected from the group consisting of anilinium cations, ammonium cations, trityl carbenimn cations, Group-11 metal cations, silylium cations, hydretes of group-1 or group-2 cations and derivatives of the foregoing anilinium, ammonium, trityl carbenium, or silylium cations containing $C_1$-$C_{20}$ hydrocarbyl, hydrocarbylsilyl, or hydrocarbylamine substituents for one or more cation hydrogen atoms.

6. The activator of claim 1 wherein the central core is tetrakis(5,6,7,8-tetrafluoro)napth-2-yl borate.

7. The activator of claim 3 wherein the first aromatic ring is distal to the boron atom.

8. The activator of claim 3 wherein the second aromatic ring is distal to the boron atom.

9. An activator having the following formula:

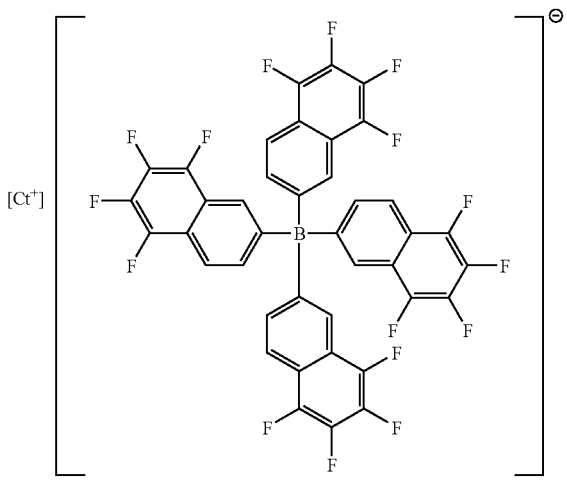

[Ct]+ is a cation that abstracts a ligand from a catalyst precursor.

10. An activator having the following formula:

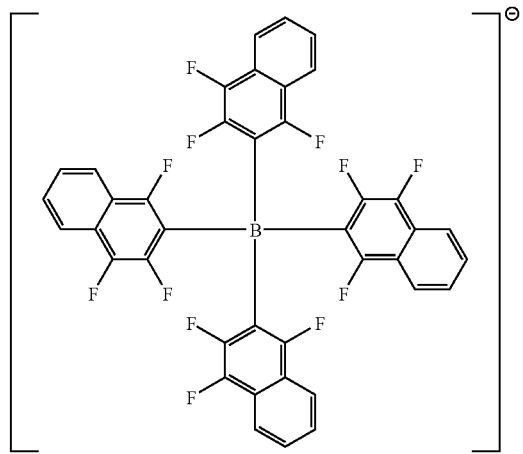

[Ct]+ is a cation that abstracts a ligand from a catalyst precursor.

11. An activator having the following formula:

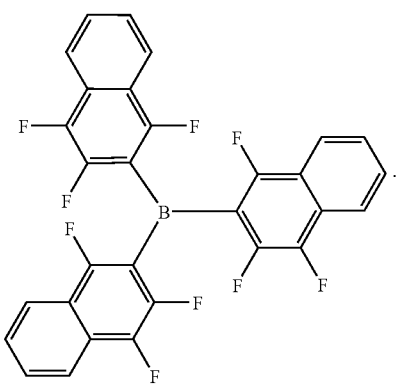

12. A catalyst system comprising
at least one transition metal olefin polymerization catalyst precursor; and
the activator of claim 3.

13. An polymerization catalyst comprising the reaction product of at least one transition metal olefin polymerization catalyst precursor and the activator of claim 3.

14. A method for producing polymer comprising
providing the catalyst of claim 13;
providing monomer(s); and
combining the catalyst and the monomer under polymerization conditions.

15. An olefin polymerization process comprising:
providing olefin monomer(s);
providing at least one transition metal olefin polymerization catalyst precursor that polymerizes olefins after activation;
providing the activator of claim 7;
contacting the at least one catalyst precursor with the activator to form at least one activated catalyst and non-coordinating anions; and
contacting the at least one activated catalyst with the olefin monomer(s).

16. An olefin polymerization process comprising:
providing olefin monomer(s);
providing at least one transition metal olefin polymerization catalyst precursor that polymerizes olefins after activation;
providing the activator of claim 8;
contacting the at least one catalyst precursor with the activator to form at least one activated catalyst and non-coordinating anions; and
contacting the at least one activated catalyst with the olefin monomer(s).

17. A method of preparing an activator comprising
(a) providing 3-bromothiophene;
(b) providing perfluorophenyl magnesium bromide;
(c) reacting the 3-bromothiophene with the perfluorophenyl magnesium bromide;
(d) reducing the product of step (c);
(e) reacting the product of step (d) with boron trichloride;
(f) reacting the product of step (e) with a quaternary ammonium chloride.

18. An olefin polymerization process comprising:
providing olefin monomer(s);
providing at least one catalyst precursor that polymerizes olefins after activation;
providing the activator produced by the method of claim 17;
contacting the at least one catalyst precursor with the activator to form at least one activated catalyst and non-coordinating anions; and
contacting the activated catalyst with the olefin monomer(s).

* * * * *